(12) United States Patent
Flohr

(10) Patent No.: US 10,335,095 B2
(45) Date of Patent: Jul. 2, 2019

(54) METHOD FOR LOCAL IMPROVEMENT OF IMAGE QUALITY

(71) Applicant: Siemens Healthcare GmbH, Erlangen (DE)

(72) Inventor: Thomas Flohr, Uehlfeld (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/225,861

(22) Filed: Aug. 2, 2016

(65) Prior Publication Data

US 2017/0053414 A1 Feb. 23, 2017

(30) Foreign Application Priority Data

Aug. 20, 2015 (DE) .......................... 10 2015 215 938

(51) Int. Cl.
*A61B 6/03* (2006.01)
*A61B 6/12* (2006.01)
(Continued)

(52) U.S. Cl.
CPC .............. *A61B 6/032* (2013.01); *A61B 6/12* (2013.01); *A61B 6/5211* (2013.01); *A61B 6/54* (2013.01); *G06T 11/005* (2013.01); *A61B 6/467* (2013.01)

(58) Field of Classification Search
CPC .......... A61B 6/04; A61B 6/587; A61B 18/12; A61B 18/20; A61B 2017/00867; A61B 2090/374; A61B 2090/3983; A61B 5/4244; A61B 6/12; A61B 6/145; A61B 6/483; A61B 6/506; A61B 6/507; A61B 6/548; A61B 90/36; A61B 6/08; A61B 6/501; A61B 6/027; A61B 6/032; A61B 6/37; A61B 6/405; A61B 6/4241; A61B 6/482; A61B 1/05; A61B 2018/0016; A61B 2018/0022; A61B 2018/00339; A61B 2018/00351; A61B 2018/00577; A61B 2018/00839; A61B 2018/0212; A61B 2562/164; A61B 2562/166; A61B 5/0024; A61B 6/486; A61B 6/5205; A61B 6/5282; A61B 5/0261; A61B 5/08; A61B 5/087; A61B 6/4007; A61B 6/4014; (Continued)

(56) References Cited

U.S. PATENT DOCUMENTS 5,825,842 A * 10/1998 Taguchi ................. A61B 6/032
378/15
6,185,336 B1 * 2/2001 Clark ................. H04N 1/40062
358/1.9
(Continued)

FOREIGN PATENT DOCUMENTS

DE 102006044783 A1 4/2008

*Primary Examiner* — Aklilu K Woldemariam
(74) *Attorney, Agent, or Firm* — Harness, Dickey & Pierce, P.L.C.

(57) ABSTRACT

A method is for local improvement of the image quality of an imaging X-ray acquisition. In an embodiment, the method includes localizing an imaging region of a structure; selecting an environment of the imaging region; setting an acquisition parameter for the environment of the imaging region, wherein the acquisition parameter for the environment of the imaging region is different from a region outside of the environment of the imaging region; and acquiring an image dataset.

34 Claims, 8 Drawing Sheets

(51) Int. Cl.
*A61B 6/00* (2006.01)
*G06T 11/00* (2006.01)

(58) Field of Classification Search
CPC ... A61B 6/4042; A61B 6/4085; A61B 6/4092; A61B 6/4233; A61B 6/4441; A61B 6/5217; A61B 6/544; A61B 2010/0077; A61B 2010/0225; A61B 2017/00022; A61B 2017/00345; A61B 34/73; A61B 5/01; A61B 5/0215; A61B 5/026; A61B 5/03; A61B 5/076; A61B 5/14546; A61B 5/411; A61B 5/418; A61B 5/6852; G01T 1/24; G01T 1/244; G01T 1/1648; G03B 42/042; G03B 42/047; G06T 2207/10116; G06T 7/0012; G06T 7/0081; G06T 3/40; G06T 11/008; G06T 2211/436; G06T 11/006; G06T 2211/412; G01N 23/20; G01N 23/20083; G01N 23/223; G01N 2223/419; G01N 23/046; G01V 5/00; G01V 5/0025; G01V 5/0041; G01V 5/0058; G01V 5/0091; G01J 1/02; G21K 7/00; H01J 2237/2813; G06F 17/18
USPC .......................... 382/128, 129, 130, 131, 132
See application file for complete search history.

(56) References Cited

U.S. PATENT DOCUMENTS

| | | | |
|---|---|---|---|
| 7,330,594 B2* | 2/2008 | Rifu | G06T 5/003 382/131 |
| 2002/0150205 A1* | 10/2002 | Adriaansz | A61B 6/032 378/54 |
| 2004/0120557 A1* | 6/2004 | Sabol | G06Q 10/10 382/128 |
| 2004/0195512 A1* | 10/2004 | Crosetto | A61B 6/037 250/363.04 |
| 2006/0146377 A1* | 7/2006 | Marshall | G06T 3/4038 358/486 |
| 2007/0189436 A1* | 8/2007 | Goto | A61B 6/032 378/4 |
| 2007/0268997 A1* | 11/2007 | Zhu | A61B 6/5282 378/7 |
| 2007/0269019 A1* | 11/2007 | Spahn | G03B 42/02 378/207 |
| 2007/0291896 A1* | 12/2007 | Parham | G01N 23/046 378/37 |
| 2008/0075225 A1 | 3/2008 | Kalender | |
| 2008/0118021 A1* | 5/2008 | Dutta | A61B 6/032 378/4 |
| 2009/0196470 A1* | 8/2009 | Carl | A61N 5/1049 382/128 |
| 2009/0310844 A1* | 12/2009 | Ludwig | A61B 6/502 382/131 |
| 2011/0107270 A1* | 5/2011 | Wang | G06F 19/3481 715/850 |
| 2011/0170757 A1* | 7/2011 | Pan | A61B 6/032 382/131 |
| 2011/0319765 A1* | 12/2011 | Gertner | A61N 7/02 600/453 |
| 2012/0002782 A1 | 1/2012 | Yoshida et al. | |
| 2013/0112874 A1* | 5/2013 | Osvath | A61B 6/486 250/311 |
| 2013/0129178 A1* | 5/2013 | Wieczorek | G06T 11/006 382/131 |
| 2013/0303884 A1* | 11/2013 | Kuntz | G06T 11/006 600/417 |
| 2014/0005533 A1* | 1/2014 | Grasruck | A61B 6/032 600/425 |
| 2014/0151563 A1* | 6/2014 | Rousso | G01T 1/1603 250/362 |
| 2014/0307847 A1* | 10/2014 | Schmidt | A61B 6/032 378/5 |
| 2015/0081262 A1* | 3/2015 | Yahil | G06F 17/18 703/2 |
| 2015/0146847 A1* | 5/2015 | Liu | G01N 23/043 378/42 |
| 2016/0183903 A1* | 6/2016 | Vandroux | A61B 6/547 600/407 |
| 2016/0292876 A1* | 10/2016 | Zhao | G06T 7/13 |
| 2017/0148156 A1* | 5/2017 | Bregman-Amitai | G06T 7/0012 |

\* cited by examiner

METHOD FOR LOCAL IMPROVEMENT OF IMAGE QUALITY

PRIORITY STATEMENT

The present application hereby claims priority under 35 U.S.C. § 119 to German patent application number DE 102015215938.8 filed Aug. 20, 2015, the entire contents of which are hereby incorporated herein by reference.

FIELD

At least one embodiment of the invention generally relates to a method for local improvement of the image quality of an imaging X-ray acquisition and/or to a medical device for performing the method.

BACKGROUND

Imaging X-ray projections can be acquired via a multiplicity of medical devices for X-ray imaging, for example computed tomography systems, C-arm angiography systems, radiography devices or mammography devices. The medical devices used for X-ray imaging include at least one X-ray source. The X-ray source illuminates an examination subject and the X-ray detector positioned behind it. The X-ray beams are partially absorbed or attenuated by the examination subject. The X-ray detector is able to detect X-ray beams that pass through the examination subject.

In current-generation computed tomography systems, X-ray detectors having a scintillator material are used for converting X-ray radiation into optical signals. The optical signals are converted into electrical signals via photodiodes. The spatial resolution is limited to 15 to 20 line pairs per cm. In addition to the constraints in relation to image quality, the possibilities for deployment in clinical applications are also limited by the restricted spatial resolution.

An improvement in image quality, in particular an improved spatial resolution, would be desirable in the imaging of small structures, for example stents in the coronary arteries, in the assessment of in-stent stenoses or in imaging during interventions using needles for example. Using needles during an intervention can lead to partial volume artifacts being generated due to the inadequate spatial resolution. The partial volume artifacts are manifested as dark streak artifacts at the tip of the needle, thereby making an accurate position determination more difficult. In present-day computed tomography systems, small structures, such as, say, stents in the coronary arteries, can be examined only up to a minimum size. The partial volume artifacts produced when needles are used during interventions can only be reduced or suppressed to an inadequate extent via software-based image corrections.

SUMMARY

The inventor has recognized that future-generation computed tomography systems having direct-converting X-ray detectors may have considerably smaller detector elements. The sides of the detector elements may have a length of 250 μm, for example. The achievable spatial resolution can amount to up to 35 line pairs or more per cm. This enables images of small structures to be recorded at an increased spatial resolution. The structures can be imaged more sharply, with improved contrast and increased spatial resolution for example. Advantageously, it will be possible to assess in-stent stenoses in particular more effectively. Partial volume artifacts caused through the use of needles during an intervention with simultaneous imaging via a computed tomography system can advantageously be reduced.

The data volume of an image dataset which allows an improved spatial resolution and for example provides a plurality of energy channels, as well as the data rate to be read out, can be increased significantly compared to current computed tomography systems having a lower spatial resolution. The sampling of a field of view having a diameter of, for example, 50 cm and small detector elements sized at, for example, 250 μm as well as the readout of a plurality of energy channels can lead to an increased data volume. In addition, outside of the structures that are to be imaged at an increased resolution, the image impression can be degraded due to a high level of image noise if the radiation dose is not increased in proportion to the increased spatial resolution.

At least one embodiment of the invention discloses a method for local improvement of the image quality of an imaging X-ray acquisition and at least one embodiment includes a medical device for performing the method which enable a local improvement in image quality in an environment of small structures, for example stents or needles.

An embodiment of the invention is directed to a method for local improvement of the image quality of an imaging X-ray acquisition and/or a medical device for performing an embodiment of the method.

At least one embodiment of the invention relates to a method for local improvement of the image quality of an imaging X-ray acquisition, the method including localizing, selecting, setting, and image acquisition. In the localizing or establishing an imaging region of a structure, the imaging region of a structure is determined. The structure can be small. The structure can be strongly absorbing, for example metallic. This localizing can be performed by a user in a survey projection (topogram) or by a computing unit that is suitable for image evaluation. In the selecting, an environment of the imaging region, an environment including the imaging region is selected. In the setting, an acquisition parameter for the environment of the imaging region, the acquisition parameter is set such that the acquisition parameter for the environment of the imaging region is different from a region outside of the environment of the imaging region. In the acquiring, an image dataset, an X-ray projection is generated using the set acquisition parameter.

An embodiment of the invention further relates to a medical device for performing an embodiment of the method, the device including an X-ray detector for acquiring an image dataset and a control unit for setting an acquisition parameter as a function of an environment of an imaging region.

According to an embodiment of the invention, the localizing of the imaging region of the structure or the selecting of the environment of the imaging region is performed by a computing unit.

The computing unit performs the localizing or selecting in an automated manner or by way of user interaction. The localizing or selecting can be performed by the user or by the computing unit. For example, an imaging region or an environment of the imaging region can be suggested with the aid of the computing unit. The user is free to accept, modify or reject the suggestion. The computing unit can access a memory unit containing different information or parameters in relation to examination scenarios or structures. The computing unit can use the information or parameters for the localization or for the selection. Advantageously, the computing unit can use information from many previously performed scenarios or examinations. Advantageously, the computing unit can perform the localization in an improved manner with the aid of image recognition software.

According to an embodiment of the invention, the medical device has a computing unit for localizing an imaging region of a structure, for selecting an environment of the imaging region or for image reconstruction.

The computing unit can perform the localizing, of selecting or of image reconstruction. The computing unit can access a memory unit containing different information or parameters relating to examination scenarios or structures. Said information or parameters can originate from earlier examinations of the same patient, comprise corresponding reference information or reference parameters that originate from comparative examinations involving other patients, be specific to particular examination or intervention scenarios, e.g. needle biopsy, catheter intervention, and similar. The computing unit can advantageously use the information or parameters for the localization, for the selection or for image reconstruction.

BRIEF DESCRIPTION OF THE DRAWINGS

Example embodiments of the invention are explained in more detail below with reference to drawings, in which.

DETAILED DESCRIPTION OF THE EXAMPLE EMBODIMENTS

Figure 1:
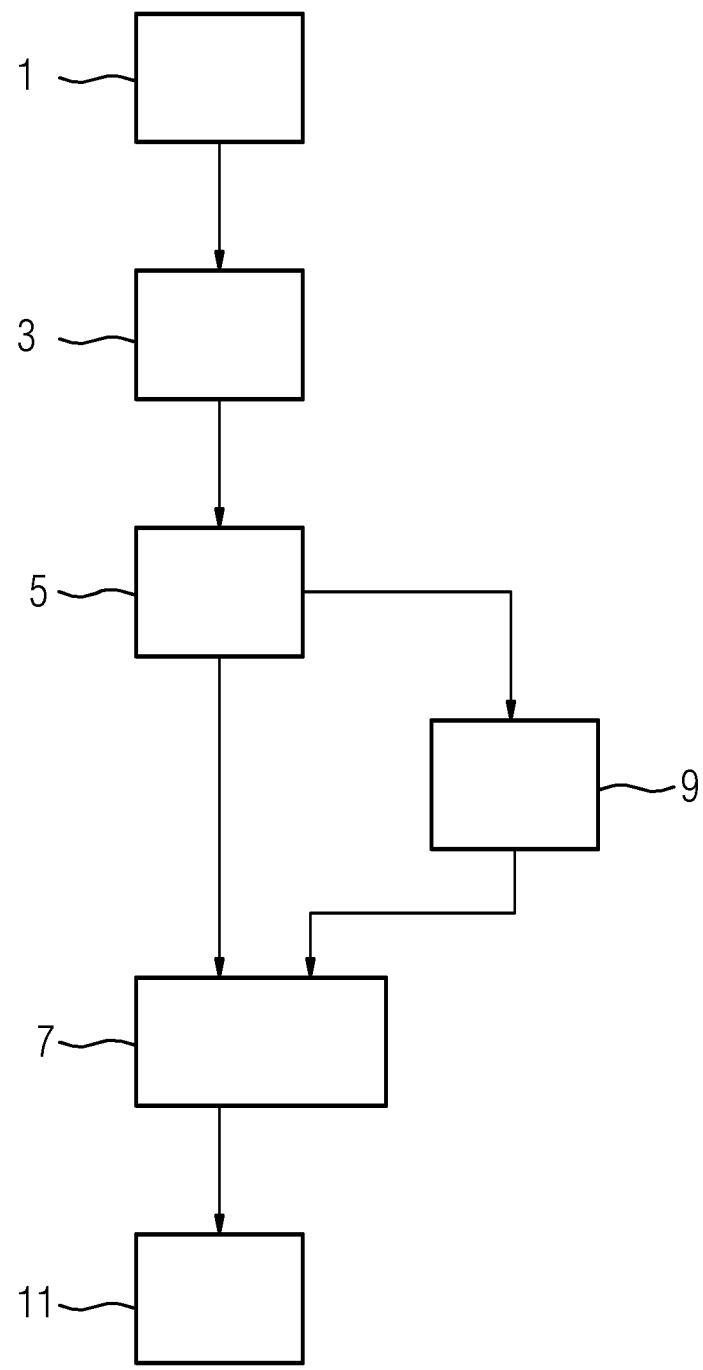
FIG. 1 schematically shows an inventive method according to a first embodiment variant.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for local improvement of the image quality of an imaging X-ray acquisition, the method including localizing, selecting, setting, and image acquisition. In the localizing or establishing an imaging region of a structure, the imaging region of a structure is determined. The structure can be small. The structure can be strongly absorbing, for example metallic. This localizing can be performed by a user in a survey projection (topogram) or by a computing unit that is suitable for image evaluation. In the selecting, an environment of the imaging region, an environment including the imaging region is selected. In the setting, an acquisition parameter for the environment of the imaging region, the acquisition parameter is set such that the acquisition parameter for the environment of the imaging region is different from a region outside of the environment of the imaging region. In the acquiring, an image dataset, an X-ray projection is generated using the set acquisition parameter.

The structure is a small structure. The size of the structure can lie in the range from 100 µm to a few cm. The diameter of the structure can amount to a few millimeters, for example. The length of the structure can amount to a few centimeters, for example. The structure can be for example a stent in a coronary artery or a needle that is used in an intervention.

In the localizing, a user can determine the imaging region, for example in a topogram or a previously acquired image dataset. The imaging region comprises the imaging of the structure. In the localizing, a computing unit can determine the imaging region, for example with the aid of image evaluation software or a position determination of the structure by way of optical markers inside or outside of the examination subject. The structure which it is intended to image at a high resolution can be localized in the field of view.

In the selecting, an environment of the imaging region is selected. The environment at least partially comprises the imaging region. The environment can at least partially comprise the imaging region and an additional region, for example at a specified or chosen distance around the imaging region. The distance from the imaging region can be predefined or selectable, a fixed distance for example. Alternatively, the environment can be selected for example such that the surface area of the environment in a two-dimensional projection is greater by a predefined or selectable percentage or relative proportion than the surface area of the imaging region.

The environment can be embodied as circular, for example. The environment can be designated as what is known as a region of interest (ROI). The environment can for example be marked or selected as circular having a radius at a predefined or selectable distance. The environment of the imaging region can be chosen such that the structure can be acquired with its closer environment in an image dataset.

An improved diagnosis or an improved localization of the structure can advantageously be achieved. The selecting can be performed by a user or by a computing unit. For structures whose position changes during the intervention from image acquisition to image acquisition or from scan to scan, the position of the structure can be detected automatically in the image by way of known methods. Differently specified distances can be used for different structures or applications.

In the setting, an acquisition parameter is set for the environment of the imaging region. A spatial resolution, spectral resolution or X-ray intensity that is changed in comparison with a region outside of the environment of the imaging region can be set. The acquisition parameter can be a reconstruction parameter. The acquisition parameter is set such that an improved local image quality is achieved in the environment of the imaging region. The acquisition parameter can be used in the step of image acquisition or after the step of image acquisition.

From the location of the imaging region and the location of the environment of the imaging region in the field of view it is possible to calculate or assign which detector region contributes to the imaging of the structure during the scan at each projection angle or each image acquisition. The environment of the imaging region can be assigned to the detector region in an assigning step. In a sinogram of the raw data, the corresponding detector region moves along a sinusoidal curve.

For each projection angle or for each image acquisition, the detector channels or detector elements located in the calculated detector region are read out or transmitted at an increased spatial resolution and/or a changed spectral resolution in comparison with a region outside of the detector region. Outside of the calculated detector region, the detector channels or detector elements are read out or transmitted at a reduced spatial resolution and/or a changed spectral resolution in comparison with the detector region. The calculated or assigned detector region can change dynamically from projection to projection or from image acquisition to image acquisition.

The transmission or the readout can be performed in such a way that the detector elements can be read out in subpixel mode inside the calculated detector region for imaging the environment of the imaging region. This means that all subpixels in the calculated detector region can be read out. This corresponds to the highest possible spatial resolution. Outside of the calculated detector region, a plurality of subpixels can be combined into a detector element or macropixel. For example, 3×3 subpixels or 4×4 subpixels can be combined. The combined information of a detector element or macropixel of said type is read out.

Alternatively, subpixels outside of the calculated region can be combined by suitable averaging or signal aggregation. Advantageously, the data volume and the data rate can be reduced compared to the readout of all subpixels of the X-ray detector. Advantageously, the readout can be adjusted dynamically according to the structure that is to be imaged.

By way of a suitably chosen environment of the imaging region it is possible to avoid or reduce partial volume artifacts at a tip of a needle without drastically increasing the data volume and without the entire image being represented with unnecessarily high image definition and with unnecessarily high image noise. In a cardiological computed tomography examination, for example, only a stent and its immediate environment can advantageously be acquired with increased image quality or image definition, without the whole heart being imaged with inappropriately high image definition and with high image noise.

In an embodiment variant in which the data rate and the data volume play a subordinate role, the X-ray detector can be read out with a uniform size of detector elements, all subpixels for example. High image noise due to inappropriately high image definition can advantageously be avoided by performing the image reconstruction at high spatial resolution in the environment of the imaging region only, and at reduced spatial resolution outside of the environment of the imaging region.

In a further embodiment variant, a movable tube-side filter can be controlled dynamically such that, for each projection angle or for each image acquisition, only the environment of the imaging region is illuminated with high photon statistics or a high radiation dose. The region outside of the environment of the imaging region is illuminated with reduced photon statistics or a reduced radiation dose. By this means it is advantageously possible for example to achieve a high spatial resolution with low image noise and improved image quality in the environment of the imaging region without significantly increasing the overall radiation dose or overall patient dose.

In the image acquisition, an image dataset is acquired, wherein the image dataset can represent a single X-ray image acquisition or a series of X-ray image acquisitions. The image dataset or the series of X-ray image acquisitions can comprise a plurality of image acquisitions or projections. The set acquisition parameter can be used for the image acquisition. The set parameter can be used for the further processing of the image dataset, for the reconstruction of an image for example. The set acquisition parameter can be a parameter of an X-ray detector, a filtering parameter or a reconstruction parameter.

The X-ray detector for acquisition of the image dataset can be an indirect-converting or a direct-converting X-ray detector. Preferably, a counting X-ray detector is used. The X-ray detector can have a plurality of detector elements in a two-dimensional array. The size of the detector elements can range from 25 µm to 1 mm. Preferably, the size of the detector elements is between 100 µm and 500 µm. The detector elements can be subpixels. A plurality of subpixels can be combined into a macropixel with the aid of a logic circuit. Preferably, the X-ray detector has a plurality of energy channels per detector element. A local changed spatial resolution or a local changed spectral resolution can be set. The spatial resolution and the spectral resolution can be set independently of one another.

An improved spatial resolution or an improved spectral resolution can advantageously be achieved in the environment of the imaging region. For example, the spatial resolution can be doubled, tripled or quadrupled inside the environment of the imaging region. An enhanced image quality can advantageously be achieved in the environment of the imaging region. An improved position determination for needles during an intervention can advantageously be performed. Partial volume artifacts can advantageously be reduced. Imaging of stents can advantageously be improved. Assessment of in-stent stenoses can advantageously be improved. A plurality of energy channels, for example four, can be read out inside the environment of the imaging region. Fewer energy channels or only the count information can be read out outside of the environment of the imaging region. The spatial resolution can in this case be the same or changed inside and outside of the environment of the imaging region. A weighting of spatial information and spectral information can advantageously be used in order to achieve an improvement in image quality. Information relating to the material composition in the environment of the imaging region can advantageously be obtained.

An embodiment of the invention further relates to a medical device for performing an embodiment of the method, the device including an X-ray detector for acquiring an image dataset and a control unit for setting an acquisition parameter as a function of an environment of an imaging region.

The control unit can set the acquisition parameter as a function of an environment of an imaging region. The control unit can set the acquisition parameter with the aid of the localization or localizing of the image acquisition region, for example in a topogram, in a prior image acquisition or by way of an optical marker. The control unit can set an acquisition parameter for the X-ray detector, for a filter or for the reconstruction. The control unit can establish the relationship between a spatial arrangement of the environment of the imaging region, for example in a topogram, and the spatial arrangement of the detector elements of an X-ray detector, of a spatial arrangement of the filter or data points in the image dataset. An assignment of the selected environment to detector elements, filter positions or data points in the image dataset can be established. The control unit can set the acquisition parameter for example for different projections, different positions of the examination subject or moving structures. A user can use the control unit for manually setting acquisition parameters.

An improved spatial resolution or an improved spectral resolution can advantageously be achieved in the environment of the imaging region by way of the medical device according to the invention. An improved image quality can advantageously be achieved in the environment of the imaging region. An improved position determination for needles during an intervention can advantageously be performed. Partial volume artifacts can advantageously be reduced. The imaging of stents can advantageously be improved. The assessment of in-stent stenoses can advantageously be improved. A weighting of spatial information and spectral information can advantageously be used in order to achieve an improvement in image quality. The medical device can advantageously perform steps of the method or support the user.

According to an embodiment of the invention, the method further comprises assigning or determining a detector region for the acquisition of images of the selected environment of the imaging region.

In the assigning, a detector region for the acquisition of images of the selected environment of the imaging region, the relationship between a spatial arrangement of the environment of the imaging region is established, for example in a topogram, and the spatial arrangement of the detector elements of an X-ray detector. An assignment of the selected environment to detector elements can be established. The assignment can be determined for example for different projections, different image acquisitions, different positions of the examination subject, or moving structures. The positions of X-ray source and X-ray detector can change for acquisitions of a series of images relative to the examination subject, for example as a result of a rotation of the gantry having the X-ray source and the X-ray detector or as a result of a translation of the examination subject or the structure. The examination subject can be moved along the axis of rotation. The position of the examination subject can be unchanged for a plurality of successive image acquisitions. The control unit or the user can perform the assigning step.

The image quality can advantageously be improved locally in spite of translations of the examination subject or the structure. The image quality can advantageously be improved in spite of rotations of the X-ray source and the X-ray detector. The data volume can advantageously be reduced by assigning a detector region for each image acquisition.

According to an embodiment of the invention, the acquisition parameter is chosen such that the spatial resolution in the environment of the imaging region is increased.

An increased spatial resolution in the environment of the imaging region can be achieved by way of the set acquisition parameter. The increased spatial resolution can advantageously be achieved in the image acquisition or the reconstructed image.

According to an embodiment of the invention, the spatial resolution of the environment of the imaging region projected onto the detector region is increased.

An increased spatial resolution can be set at the X-ray detector by way of the set acquisition parameter. Smaller detector elements can be read out in a detector region assigned to the selected environment of the imaging region. For example, subpixels can be read out in the detector region assigned to the selected environment of the imaging region, while macropixels can be read out in a further detector region assigned to the region outside of the environment of the imaging region. For example, a few combined subpixels can be read out in the detector region assigned to the selected environment of the imaging region, while a plurality of combined subpixels can be read out in the further detector region assigned to the region outside of the environment of the imaging region. The X-ray detector can advantageously record the environment of the imaging region at a locally increased spatial resolution.

According to an embodiment of the invention, the acquisition parameter is chosen such that the spectral resolution in the environment of the imaging region is changed.

An increased spectral resolution in the environment of the imaging region can be achieved by way of the set acquisition parameter. The increased spectral resolution can advantageously be achieved in the image acquisition or the reconstructed image. A weighting of position information and energy information can advantageously be used in order to improve the image quality or to differentiate materials in the environment of the imaging region.

According to an embodiment of the invention, the spectral resolution of the environment of the imaging region projected onto the detector region is changed.

An increased spectral resolution can be set at the X-ray detector by way of the set acquisition parameter. In a detector region assigned to the selected environment of the imaging region, more or fewer energy channels can be read out per detector element. For example, more energy channels can be read out in the detector region assigned to the selected environment of the imaging region, while fewer energy channels can be read out in a further detector region assigned to the region outside of the environment of the imaging region. The X-ray detector can advantageously record the environment of the imaging region at a locally increased spectral resolution. The setting of a changed spectral resolution can be combined with an increased spatial resolution.

According to an embodiment of the invention, the localizing of the imaging region of the structure or the selecting of the environment of the imaging region is performed by a user.

The user can perform the step of localizing, for example via an output device and an input device. The user can perform the step of selecting, for example via an output device and an input device. A practiced, experienced or trained user can localize the imaging region of the structure. A practiced, experienced or trained user can select the environment of the imaging region. Advantageously, the user can apply his or her experience for the localization or use further information in the decision for the localization.

According to an embodiment of the invention, the localizing of the imaging region of the structure or the selecting of the environment of the imaging region is performed by a computing unit.

The computing unit performs the localizing or selecting in an automated manner or by way of user interaction. The localizing or selecting can be performed by the user or by the computing unit. For example, an imaging region or an environment of the imaging region can be suggested with the aid of the computing unit. The user is free to accept, modify or reject the suggestion. The computing unit can access a memory unit containing different information or parameters in relation to examination scenarios or structures. The computing unit can use the information or parameters for the localization or for the selection. Advantageously, the computing unit can use information from many previously performed scenarios or examinations. Advantageously, the computing unit can perform the localization in an improved manner with the aid of image recognition software.

According to an embodiment of the invention, the method further comprises an image reconstruction for reconstructing an image from the image dataset, wherein the acquisition parameter is a reconstruction parameter.

For the image reconstruction, the image dataset from the image acquisition is used for reconstructing an image. The image dataset can be a raw data set of the X-ray detector. The image can be reconstructed as a sectional image or slice, as a three-dimensional image or as a four-dimensional image. The acquisition parameter can be a reconstruction parameter. The reconstruction parameter can be used for setting a spatial resolution or a spectral resolution. Furthermore, the reconstruction parameter can contain the information concerning the setting of the acquisition parameter of the X-ray detector or of the filter and the reconstruction parameter can be used during the reconstruction. For example, the achievable spatial resolution or spectral resolution can advantageously be determined from the assignment of the environment of the imaging region to the detector region. The assignment of the environment of the imaging region to the detector region or the set acquisition parameter can advantageously be used in reconstruction algorithms, for example in frequency filters or convolution kernels.

According to an embodiment of the invention, the setting of the acquisition parameter comprises the use of a filter.

A filter placed in front of the X-ray source can be used. The filter is adjustable and can advantageously be moved in front of the X-ray source. The filter can advantageously attenuate the X-ray radiation. Inside the environment of the imaging region, the radiation dose or the X-ray intensity can be ten times as high as outside of the environment of the imaging region.

According to an embodiment of the invention, the filter is set in such a way that an X-ray intensity in the region outside of the environment of the imaging region is reduced.

The filter is adjustable and a reduced intensity of the X-ray radiation can be achieved in the region outside of the environment of the imaging region. The filter can attenuate the X-ray radiation outside of the environment of the imaging region and advantageously increase the intensity of the X-ray radiation in the environment of the imaging region. The radiation dose in the region outside of the environment of the imaging region can advantageously be reduced. The radiation dose outside of the environment of the imaging region can advantageously be the same or barely increased compared to a conventional, locally unenhanced image quality. A better resolution can advantageously be achieved in the environment of the imaging region.

According to an embodiment of the invention, the medical device further comprises a segmentation unit for determining or assigning a detector region for the acquisition of images of the selected environment of the imaging region.

The segmentation unit can determine or assign the detector region at increased spectral resolution or spatial resolution for example. The segmentation unit can perform the step of assigning. The segmentation unit can define an assignment between the environment of the imaging region and the detector region, the detector elements as well as the acquisition parameters. For example, the segmentation unit can advantageously determine or assign the detector region for different projections or image acquisitions. The image quality can advantageously be improved for all projections or a series of image acquisitions in the environment of the imaging region. The segmentation unit can be part of the computing unit.

According to an embodiment of the invention, the medical device has a computing unit for localizing an imaging region of a structure, for selecting an environment of the imaging region or for image reconstruction.

The computing unit can perform the localizing, of selecting or of image reconstruction. The computing unit can access a memory unit containing different information or parameters relating to examination scenarios or structures. The information or parameters can originate from earlier examinations of the same patient, comprise corresponding reference information or reference parameters that originate from comparative examinations involving other patients, be specific to particular examination or intervention scenarios, e.g. needle biopsy, catheter intervention, and similar. The computing unit can advantageously use the information or parameters for the localization, for the selection or for image reconstruction.

According to an embodiment of the invention, the medical device comprises an output device for the localization of the imaging region by a user or an input device for the selection of the environment of the imaging region by a user.

The output device can be a screen. The input device can be a keyboard, a touchpad, a gesture recognition device or a voice control device. The user can advantageously localize the imaging region based on his or her experiences. The user can advantageously select the environment based on his or her experience. The user can advantageously accept, modify or reject suggestions of the computing unit with regard to the localization, the selection or the setting. When selecting the environment, the user can advantageously select from a number of suggestions which differ for example in respect of the size of the additional region that extends beyond the imaging region. Thus, the user has the option to choose a narrower or wider environment of the imaging region from a number of corresponding suggestions provided by the computing unit.

According to an embodiment of the invention, the spatial resolution or the spectral resolution of the X-ray detector can be set differently in the detector region for the acquisition of images of the selected environment of the imaging region and in a wider detector region for the acquisition of images of a region outside of the environment of the imaging region.

The X-ray detector has an adjustable spatial resolution or an adjustable spectral resolution. The spatial resolution and the spectral resolution can be adjustable locally. The detector region and the wider detector region can be determined by the computing unit or by the user. A locally improved image quality can advantageously be achieved. Advantageously, the data volume and the data rate can be controlled.

According to an embodiment of the invention, a filter reduces an X-ray intensity in the region outside of the environment of the imaging region. The filter is mounted between the X-ray source and the examination subject. The filter enables an increased X-ray intensity in the environment of the imaging region, e.g. in that the filter allows a local change in the X-ray intensity over different regions of an object or a patient to be examined. Advantageously, the structure and the environment of the imaging region can be examined with higher photon statistics. The filter can contain aluminum or Teflon, for example.

The filter can include movable blades. Two rows of blades disposed opposite one another can be used. The blades are elongate. The blades can be displaced along the longitudinal axis. Oppositely disposed blades of the oppositely disposed blades can provide a continuous filtering. Adjacent blades have an overlapping area intended for the purpose of homogenizing the attenuation. The blades can be moved independently of one another. A contiguous area of reduced attenuation can advantageously be set. The contiguous area can advantageously comprise the environment of the imaging region.

In one embodiment variant, a single blade or diaphragm can be disposed opposite another in each case. On the side disposed opposite the other blade, the blades can have a cutout in the shape of a segment or sector of a circle. The two single oppositely disposed blades or diaphragms can advantageously attenuate the X-ray intensity outside of the environment of the imaging region. In a further embodiment variant, the filter can comprise an iris diaphragm.

The filter can be embodied as what is known as a bowtie filter. In cross-section along the central beam of the X-ray source, the filter forms the shape of a bowtie. The filter can be embodied as symmetric, such that a small material thickness is present in the middle of the filter. The thickness of the material increases toward the sides. The filter can be embodied as radially symmetric. The filter can advantageously be set such that the photon statistics outside of the environment of the imaging region are reduced and the environment of the imaging region can be examined or imaged with higher photon statistics. An unduly increased radiation dose outside of the environment of the imaging region is advantageously avoided.

According to an embodiment of the invention, the medical device is a computed tomography system or a C-arm angiography system.

Medical devices embodied as computed tomography or C-arm angiography systems can use a plurality of projections for reconstructing slice images, three-dimensional images or four-dimensional images. A computed tomography or C-arm angiography system can be used before, during or after interventions on the examination subject, for example using needles or stents that are to be localized. The image quality can advantageously be improved locally in slice image acquisitions. In-stent stenoses, stents or needles can advantageously be visualized with an improved image quality.

FIG. 1 shows an example implementation of an inventive method according to a first embodiment variant. The method for local improvement of the image quality of an imaging X-ray acquisition comprises localizing 1, selecting 3, setting 5, and image acquisition 7. In the localizing 1, an imaging region 15 of a structure, the imaging region 15 of a structure is determined. The structure is a small structure. The size of the structure lies in the range of 100 μm to a few cm. The diameter of the structure amounts to a few millimeters for example. The length of the structure amounts to a few centimeters for example. The structure is for example a stent in a coronary artery or a needle that is used in an intervention. The localizing 1 is performed by a user in a topogram or by a computing unit with the aid of image evaluation software, or in combination. In the step of localizing 1, a user determines the imaging region 15, for example in a topogram or a prior image acquisition. In the localizing 1, a computing unit 95 alternatively determines the imaging region 15, for example with the aid of image evaluation software or a position determination of the structure by way of optical markers inside or outside of the examination subject 89.

In the selecting 3, an environment 17 of the imaging region 15, an environment 17 including the imaging region 15 is selected. The environment 17 comprises the imaging region 15 and an additional region, for example at a specified or chosen distance around the imaging region 15. The distance of the outer limits of the environment 17 from the outer limits of the imaging region 15 can be chosen as a fixed distance and amounts for example to 2 cm. The environment 17 is embodied as circular or elliptical, for example. The environment 17 is marked or selected for example as circular with a radius of 2 cm. The environment 17 of the imaging region 15 can be chosen such that the structure can be acquired together with its closer environment 17 in an image dataset. The step of selecting 3 can be performed by a user or by the computing unit 95. Differently specified distances can be used for different structures or applications.

In the setting 5, an acquisition parameter for the environment 17 of the imaging region 15, the acquisition parameter is set such that the acquisition parameter for the environment 17 of the imaging region 15 is different from a region outside of the environment 17 of the imaging region 15. A spatial resolution, spectral resolution or intensity that is changed in comparison with a region outside of the environment 17 of the imaging region 15 is set.

The acquisition parameter is alternatively a reconstruction parameter. For example, the X-ray detector 79 is read out at a uniform spatial resolution and in the step of image reconstruction an image is reconstructed with a changed spatial resolution in the environment of the imaging region. The acquisition parameter is set such that an improved local image quality is achieved in the environment 17 of the imaging region 15.

In the acquisition 7 of an image dataset, an X-ray image dataset is acquired using the set acquisition parameter. The image dataset represents a single X-ray image acquisition or a series of X-ray image acquisitions. The set acquisition parameter can be used for the image dataset acquisition. The set parameter can be used for further processing of the image dataset, for example for the reconstruction of an image. The set acquisition parameter is a parameter of an X-ray detector 79, a filter 75 or an image reconstruction 11.

In a variant embodiment, the method can comprise assigning 9 a detector region for the acquisition of images of the selected environment 17 of the imaging region 15 between the setting 5 and the image acquisition 7. In the assigning 9, the relationship between a spatial arrangement of the environment 17 of the imaging region 15, for example in a topogram, and the spatial arrangement of the detector elements of an X-ray detector 79 is established. An assignment of the selected environment 17 to detector elements can be established. The assignment can be determined for example for different projections, different positions of the examination subject 89 or moving structures. The control unit 71 or the user can perform the step of assigning 9.

In a variant embodiment, the method can comprise image reconstruction 11 after the image acquisition 7. In the image reconstruction 11, an image is reconstructed from the image dataset. For the image reconstruction, the image dataset from the image acquisition 7 is used for reconstructing an image. The image can be reconstructed as a slice image, as a three-dimensional image or as a four-dimensional image. The acquisition parameter can be a reconstruction parameter. The reconstruction parameter contains the information concerning the setting 5 of the acquisition parameter of the X-ray detector 79 or of the filter 75 and the reconstruction parameter can be used during the image reconstruction 11. For example, the achievable spatial resolution or spectral resolution can be determined from the assignment of the environment 17 of the imaging region 15 to the detector region and used in reconstruction algorithms, for example in frequency filters or convolution kernels.

Figure 2:
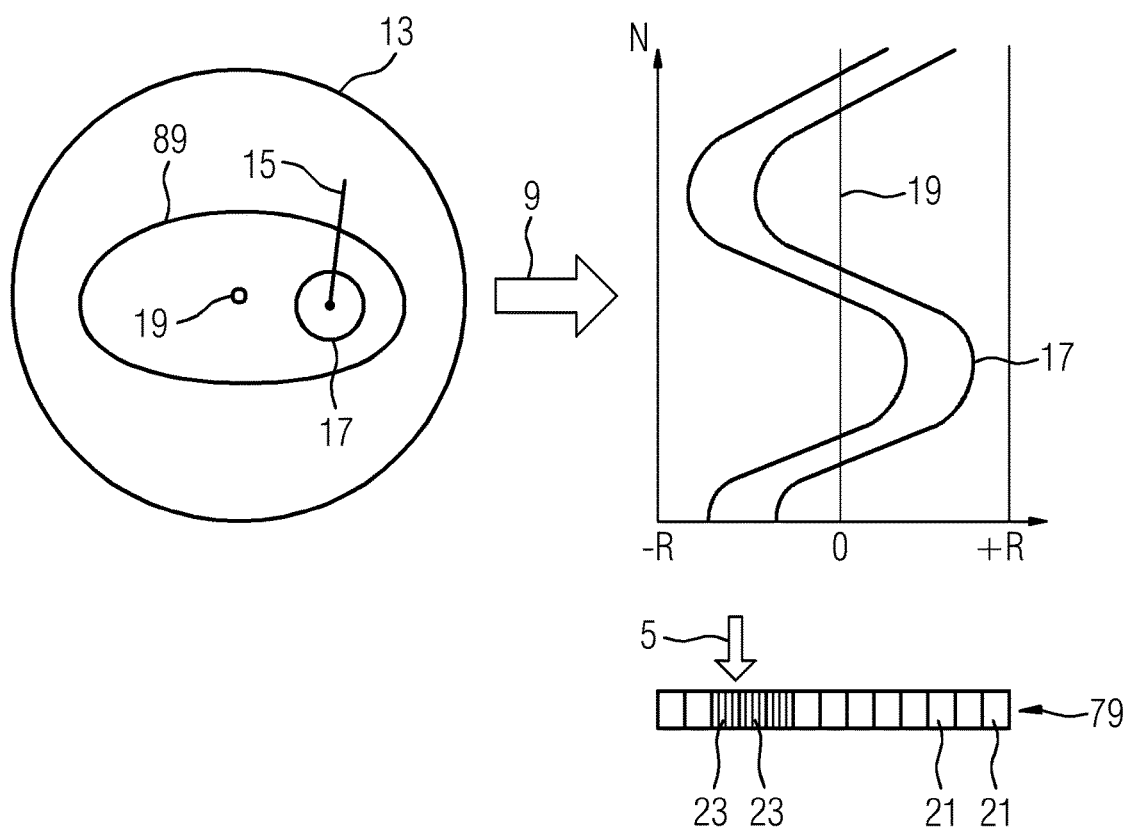
FIG. 2 schematically shows an inventive method according to a second embodiment variant.

FIG. 2 shows an example implementation of an inventive method according to a second embodiment variant. A field of view 13 having a radius R is used in order to acquire a series of slice images. At its center, the field of view 13 has the isocenter 19. The examination subject 89 is at least partially encompassed by the field of view 13. A needle is located as a structure in the examination subject 89 during an intervention. The needle is imaged in the imaging region 15 for example in a prior image acquisition.

An environment 17 around the imaging region 15 is selected. The environment 17 encompasses the imaging region 15. The relationship between imaging region 17 and detector region of the X-ray detector 79 is determined or established in the assigning 9. The detector region of the X-ray detector 79 has at least one width in the plane of rotation which comprises a span for acquisition of images of the field of view 13 from −R to R. The isocenter 19 is imaged onto a central detector element, for example a subpixel 23 or macropixel 21. The relationship between the environment 17 and the detector elements of the X-ray detector 79 is determined for all N projections. In the step of setting 5, the spatial resolution of the X-ray detector 79 is set in such a way that the environment 17 is acquired at a higher resolution than a region outside of the environment 17. The higher resolution can be realized for example by readout of the subpixels 23. The lower resolution can be realized by readout of the macropixels 21. Alternatively, different numbers of subpixels 23 can be combined so that the environment 17 is acquired at a higher resolution.

Figure 3:
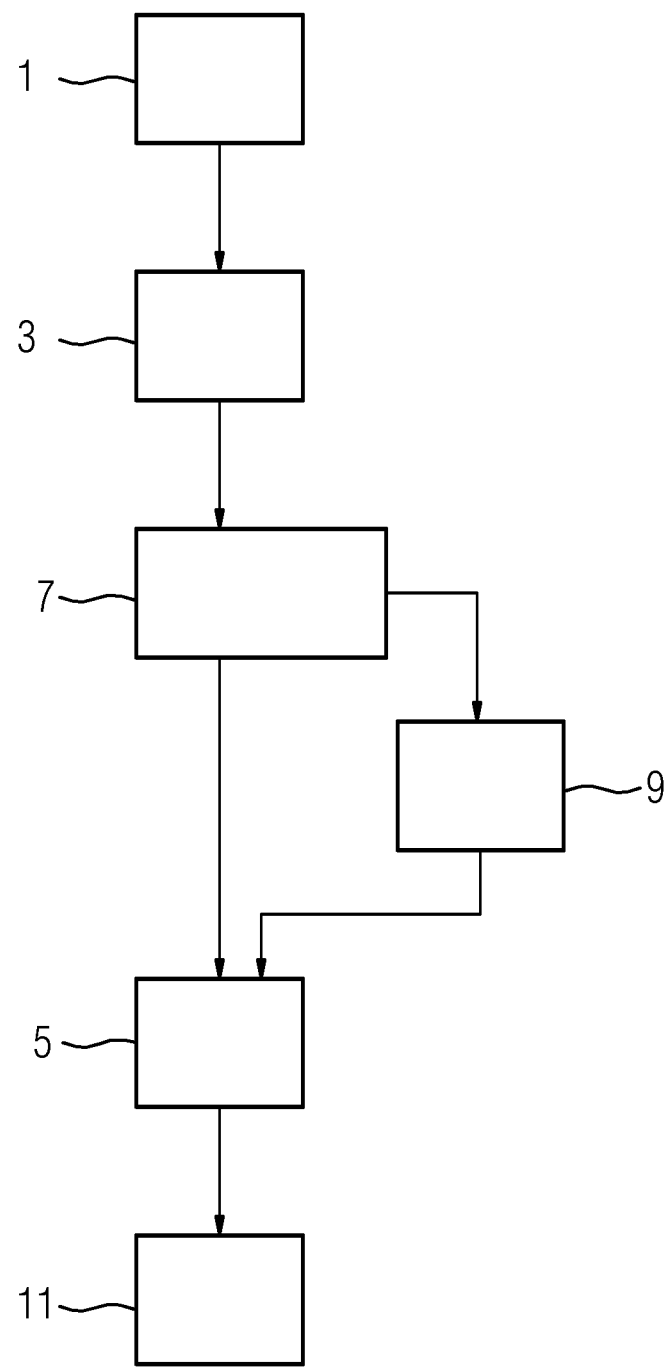
FIG. 3 schematically shows an inventive method according to a third embodiment variant.

FIG. 3 shows an example implementation of an inventive method according to a third embodiment variant.

The localizing 1 and selecting 3 are followed by the image acquisition 7. In the image acquisition 7, an image dataset is acquired, wherein the image dataset represents a single X-ray image acquisition or a series of X-ray image acquisitions. In the setting 5, an acquisition parameter for the environment 17 of the imaging region 15 is set, wherein the acquisition parameter is a reconstruction parameter.

A spatial resolution or spectral resolution that is changed in comparison with a region outside of the environment 17 of the imaging region 15 is set. The acquisition parameter is set such that an improved local image quality is achieved in the environment 17 of the imaging region 15. In the image reconstruction 11, an image is reconstructed from the image dataset. For the reconstruction of an image, the image dataset from the image acquisition 7 is used for reconstructing the image. The image can be reconstructed as a slice image, as a three-dimensional image or as a four-dimensional image. The acquisition parameter is a reconstruction parameter. The reconstruction parameter influences the spatial resolution or spectral resolution that is achievable as a result of the image reconstruction 11 in the environment 17 and outside of the environment 17. For example, an increased spatial resolution or a changed spectral resolution is set in the environment 17 of the imaging region 15 to the detector region.

In a variant embodiment, the method can comprise the assigning 9 a detector region for the acquisition of images of the selected environment 17 of the imaging region 15 between the image acquisition 7 and the setting 5. The relationship between a spatial arrangement of the environment 17 of the imaging region 15, for example in a topogram, and the spatial arrangement of the detector elements of an X-ray detector 79 is established in the step of assigning 9. An assignment of the selected environment 17 to detector elements can be established. The assignment can be determined for example for different projections, different positions of the examination subject 89 or moving structures. The control unit 71 or the user can perform the step of assigning 9. The assignment of the detector elements to the environment 17 of the imaging region 15 can be performed in the image dataset from the image acquisition step. The setting 5 of the acquisition parameter is performed in the following step on the basis of the assignment.

Figure 4:
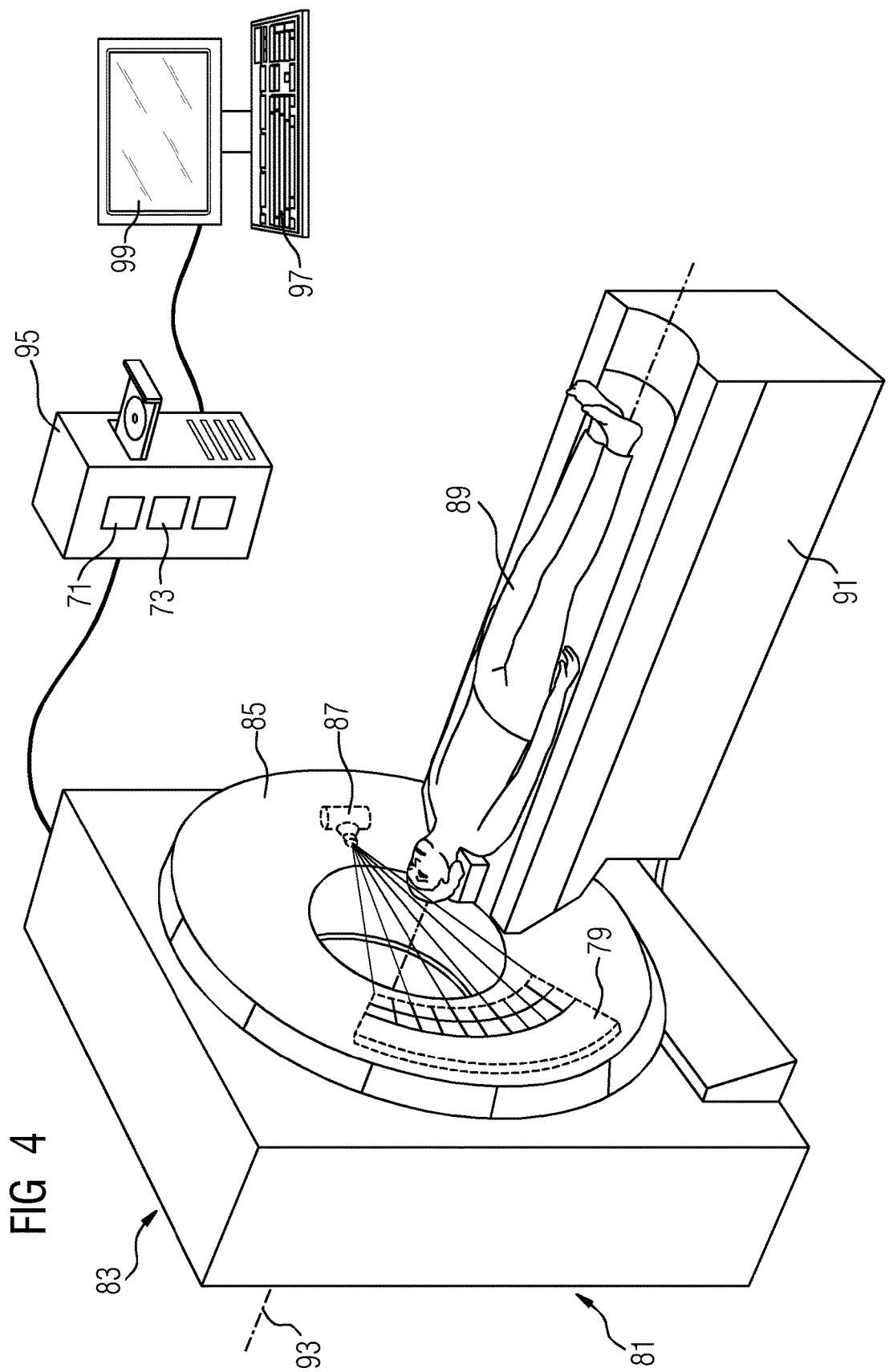
FIG. 4 schematically shows an inventive computed tomography system according to a first embodiment variant.

FIG. 4 shows an example implementation of an inventive computed tomography system 81 according to a first embodiment variant. The X-ray detector 79 can have a number of detector modules comprising a multiplicity of detector elements. Preferably, the X-ray detector 79 has a plurality of detector subunits comprising a plurality of detector elements in a two-dimensional array or arrangement. The detector elements are macropixels 21 and/or subpixels 23. The computed tomography system 81 includes a gantry 83 having a rotor 85. The rotor 85 comprises an X-ray source 87 and the X-ray detector 79. The examination subject 89, for example a patient or human being, is supported and positioned on the patient couch 91 and can be moved through the gantry 83 along the axis of rotation z 93. A computing unit 95 is used for controlling and calculating the slice images or, as the case may be, the image reconstruction 11. An input device 97 and an output device 99 are connected to the computing unit 95. The computing unit 95 has a control unit 71 and a segmentation unit 73.

Figure 5:
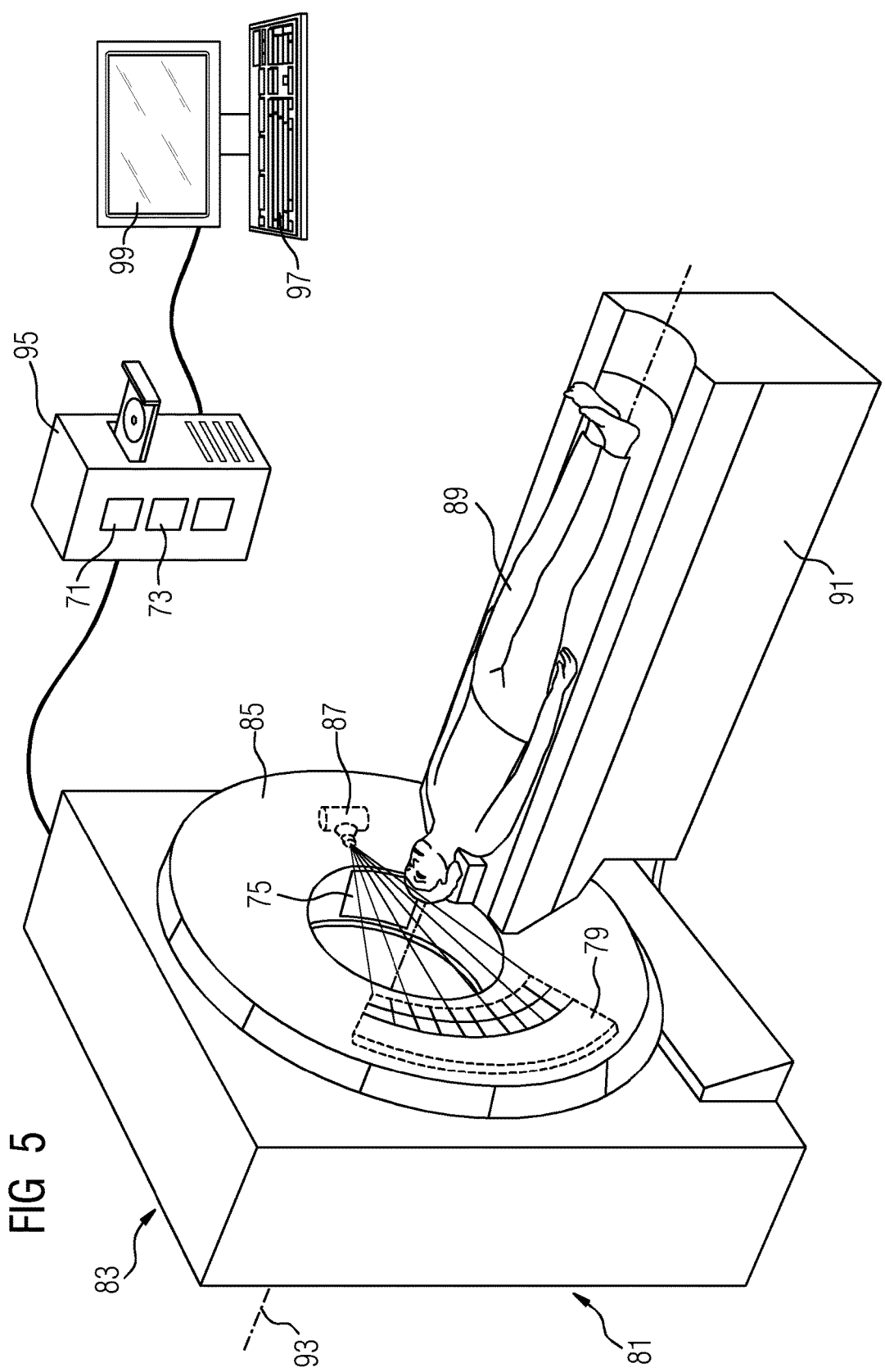
FIG. 5 schematically shows an inventive computed tomography system according to a second embodiment variant.

FIG. 5 shows an example implementation of an inventive computed tomography system 81 according to a second embodiment variant. The computed tomography system 81 further comprises a filter 75 placed in front of the X-ray source 87. The rotor 85 comprises the filter 75.

Figure 6:
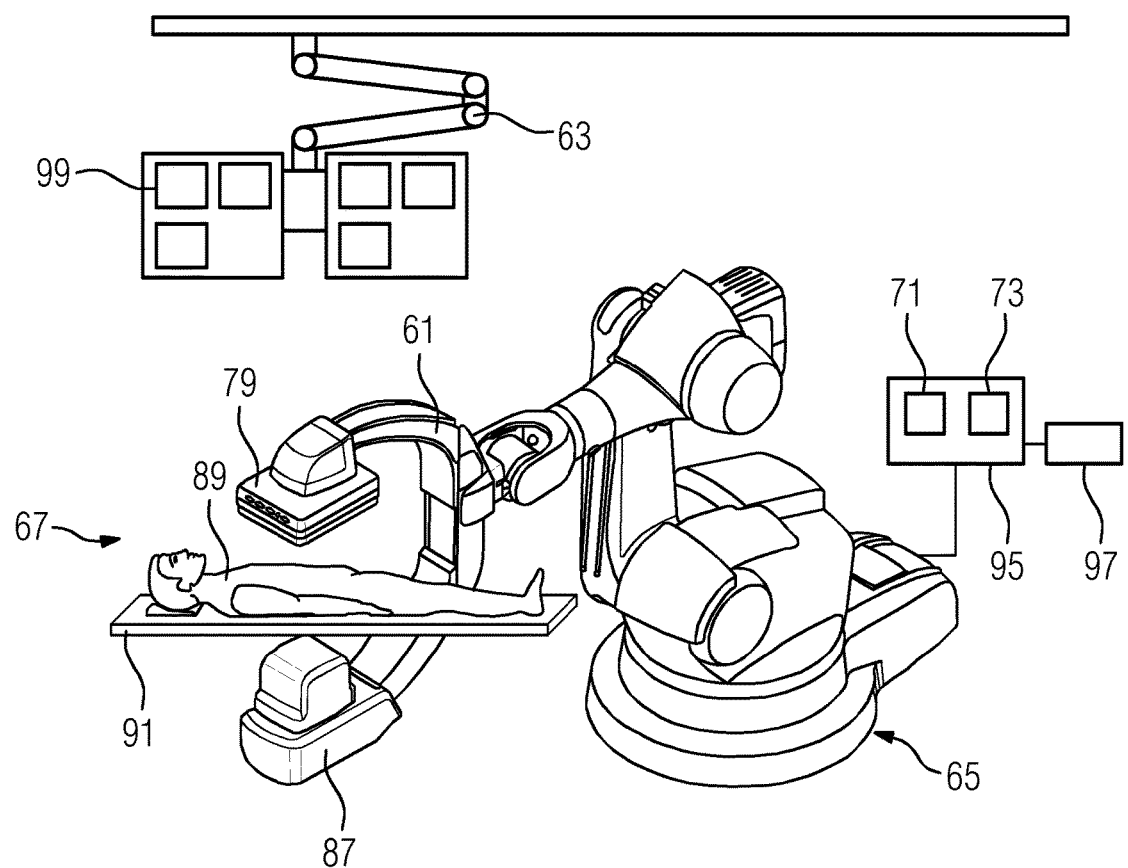
FIG. 6 schematically shows an inventive C-arm angiography system.

FIG. 6 shows an example implementation of an inventive C-arm angiography system 67. The C-arm angiography system 67 has a pedestal 65, for example in the form of an industrial robot, having a C-arm 61 held by the pedestal 65. Mounted at the ends of the C-arm 61 are an X-ray source 87 and the X-ray detector 79 as image acquisition unit. The C-arm 61 can be positioned via the degrees of freedom provided by the pedestal 65. A patient to be examined is disposed as the examination subject 89 on the patient couch 91 in the beam path of the X-ray source 87. A computing unit 95 having a high-voltage generator for generating the tube voltage and an image system is connected to the C-arm angiography system 67. The image system receives and processes the image datasets of the X-ray detector 79. The images can then be viewed on displays of an output device 99 suspended via a ceiling-mounted carrier system 63. In this configuration, the carrier system 63 has displacement, pan-and-tilt and/or height-adjusting units. A control unit 71 and a segmentation unit 73 are also provided in the computing unit. In a further embodiment variant, the C-arm angiography system 67 can have a filter 75 (not shown) placed in front of the X-ray source 87.

Figure 7:
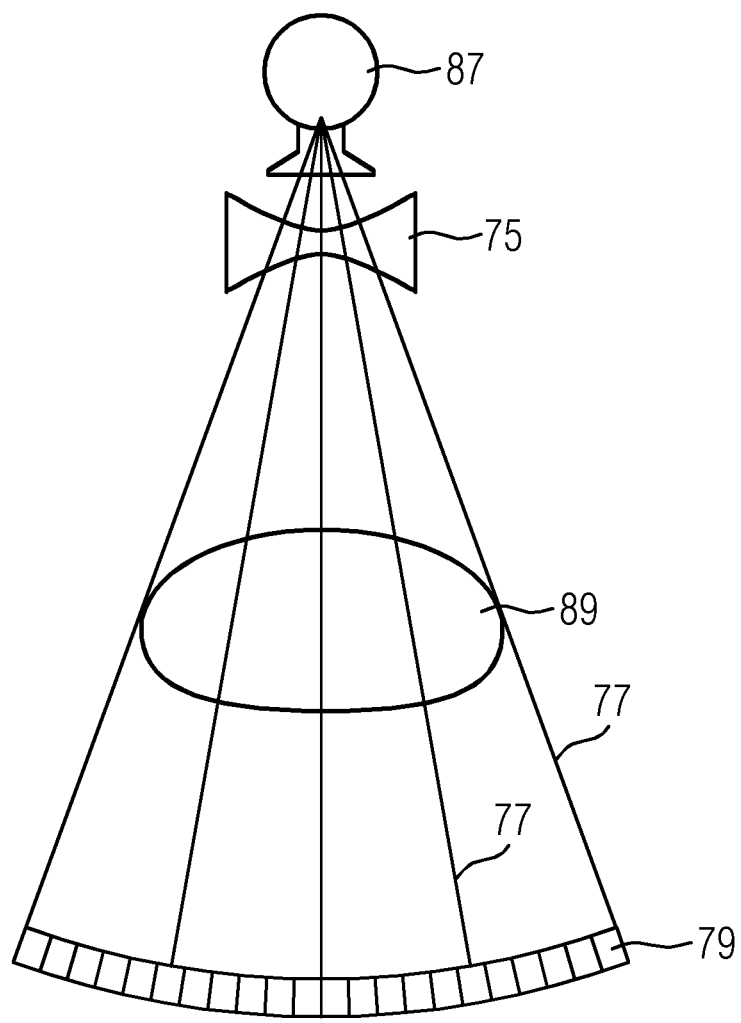
FIG. 7 schematically shows an inventive filter according to a first embodiment variant.

FIG. 7 shows an example implementation of an inventive filter 75 according to a first embodiment variant. The filter 75 can be embodied as what is known as a bowtie filter. In cross-section along the central beam of the X-ray source 87, the filter forms the shape of a bowtie. The filter 75 can be embodied as symmetric, such that a small material thickness is present in the middle of the filter 75. The thickness of the material increases toward the sides. The filter 75 can be embodied as radially symmetric. The filter 75 contains aluminum or Teflon, for example. The filter 75 can be movable in a retainer (not shown) such that an attenuation of the intensity of the X-ray radiation outside of the environment 17 of the imaging region 15 can be set. The X-ray beams 77 impinge on the examination subject 89. The X-ray beams 77 that pass through the examination subject 89 can be detected via the X-ray detector 79. The image acquisition has higher photon statistics in the environment 17 of the imaging region 15. A higher spatial resolution and/or higher spectral resolution are/is achieved in the environment 17 of the imaging region 15 at the same time as low image noise and good image quality. The filter 75 enables the setting 5 of a less strongly attenuated region 78 in the environment 17 of the imaging region 15.

Figure 8:
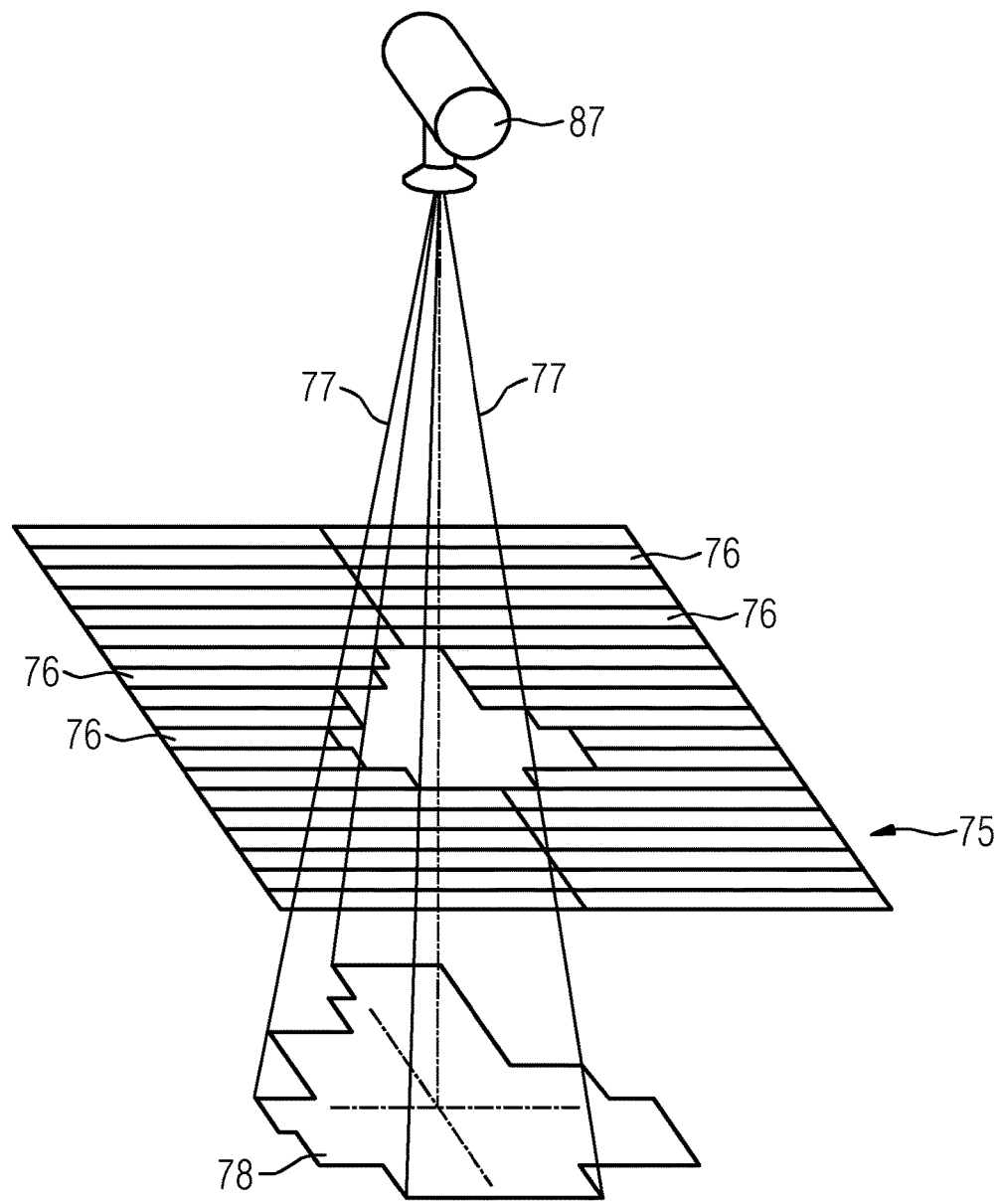
FIG. 8 schematically shows an inventive filter according to a second embodiment variant.

FIG. 8 shows an example implementation of an inventive filter 75 according to a second embodiment variant. The filter 75 includes movable blades 76. The filter 75 has two rows of blades 76 disposed opposite one another. The blades 76 are elongate. The blades 76 are arranged in a row in such a way that the long sides of the blades are adjacent within a row. The short sides of the blades 76 of one row are disposed opposite the short sides of the blades 76 of the other row. The blades 76 can be displaced along the longitudinal axis of the blades 76. In a closed position, oppositely disposed blades 76 can collectively provide continuous filtering or attenuation.

Along their long side and along their short side, adjacent blades 76 have an overlapping area intended for the purpose of homogenizing the attenuation. The blades 76 can be moved independently of one another. A contiguous aperture can be set. Some of the X-ray beams 77 of the X-ray source 87 can pass unattenuated through the aperture of the filter 75. Another portion of the X-ray beams 77 is attenuated by the blades 76. The filter 75 enables the setting 5 of an unattenuated or less strongly attenuated region 78. With the aid of the unattenuated or less strongly attenuated region 78, the environment 17 of the imaging region 15 or of the structure is irradiated by a higher number of photons.

The filter 75 contains aluminum or Teflon, for example. The image acquisition has higher photon statistics in the environment 17 of the imaging region 15. A higher spatial resolution and/or higher spectral resolution are/is achieved in the environment 17 of the imaging region 15 at the same time as low image noise and good image quality.

Although the invention has been illustrated in greater detail on the basis of the preferred example embodiment, the invention is not limited by the disclosed examples and other variations can be derived herefrom by the person skilled in the art without leaving the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for local improvement of image quality of an imaging X-ray acquisition, the method comprising:
    localizing an imaging region of a structure;

selecting an environment of the imaging region of the structure, the environment being a portion of a field of view and including at least a portion of the imaging region and an additional region adjacent to the at least the portion of the imaging region;

setting a first acquisition parameter for the environment, the first acquisition parameter having a value different from a value of a second acquisition parameter for a remainder of the field of view exclusive of the environment, both of the first acquisition parameter and the second acquisition parameter being configured to change at least one of a spatial resolution or a spectral resolution; and acquiring an image dataset using the first acquisition parameter.

2. The method of claim 1, further comprising:
assigning a detector region for acquiring image data for the environment of the imaging region of the structure.

3. The method of claim 2, wherein the first acquisition parameter is configured to increase the spatial resolution in the environment of the imaging region of the structure.

4. The method of claim 3, wherein the setting increases the spatial resolution in the environment of the imaging region of the structure projected onto the detector region.

5. The method of claim 2, wherein the first acquisition parameter is configured to change the spectral resolution in the environment of the imaging region of the structure.

6. The method of claim 5, wherein the setting changes the spectral resolution in the environment of the imaging region of the structure projected onto the detector region.

7. The method of claim 1, wherein the localizing an imaging region of a structure or the selecting an environment of the imaging region of the structure is performed based upon an action of a user.

8. The method of claim 1, wherein the localizing an imaging region of a structure or the selecting an environment of the imaging region of the structure is performed by a computing unit.

9. The method of claim 1, further comprising:
reconstructing an image based on the image dataset, wherein the first acquisition parameter is a reconstruction parameter.

10. The method of claim 1, wherein the setting a first acquisition parameter comprises using a filter.

11. The method of claim 10, wherein the filter is set to reduce an X-ray intensity in the remainder of the field of view.

12. A medical device, comprising:
an X-ray detector configured to acquire an image dataset using a first acquisition parameter;
a memory having computer-readable instructions stored thereon; and
at least one processor communicatively coupled to the memory and the X-ray detector, the at least one processor configured to execute the computer-readable instructions to
set the first acquisition parameter as a function of an environment of an imaging region of a structure, the environment being a portion of a field of view and including at least a portion of the imaging region and an additional region adjacent to the at least the portion of the imaging region, the first acquisition parameter having a value different from a value of a second acquisition parameter for a remainder of the field of view exclusive of the environment, both of the first acquisition parameter and the second acquisition parameter being configured to change at least one of a spatial resolution or a spectral resolution.

13. The medical device of claim 12, wherein the at least one processor is further configured to execute the computer-readable instructions to assign a detector region for acquiring image data for the environment of the imaging region of the structure.

14. The medical device of claim 12, wherein the at least one processor is further configured to execute the computer-readable instructions to
localize the imaging region of the structure to select the environment of the imaging region of the structure, or to reconstruct an image based on the image dataset.

15. The medical device of claim 12, further comprising:
an input or output device configured to at least one of localize the imaging region of the structure or select the environment of the imaging region of the structure.

16. The medical device of claim 13, wherein the spatial resolution or the spectral resolution of the X-ray detector is different in the detector region for acquiring the image data for the environment of the imaging region of the structure and in a further detector region for acquiring image data for the remainder of the field of view.

17. The medical device of claim 12, further comprising:
a filter configured to reduce an X-ray intensity in the remainder of the field of view.

18. The medical device of claim 12, wherein the medical device is a computed tomography system or a C-arm angiography system.

19. The method of claim 1, wherein the first acquisition parameter is configured to increase the spatial resolution in the environment of the imaging region of the structure.

20. The method of claim 1, wherein the first acquisition parameter is configured to change the spectral resolution in the environment of the imaging region of the structure.

21. The method of claim 2, wherein the localizing an imaging region of a structure or the selecting an environment of the imaging region of the structure is performed based upon an action of a user.

22. The method of claim 2, wherein the localizing an imaging region of a structure or the selecting an environment of the imaging region of the structure is performed by a computing unit.

23. The method of claim 2, further comprising:
reconstructing an image based on the image dataset, wherein the first acquisition parameter is a reconstruction parameter.

24. The method of claim 2, wherein the setting a first acquisition parameter comprises using a filter.

25. The method of claim 24, wherein the filter is set to reduce an X-ray intensity in the remainder of the field of view.

26. The medical device of claim 13, wherein the at least one processor is further configured to execute the computer-readable instructions to
localize the imaging region of the structure to select the environment of the imaging region of the structure, or to reconstruct an image based on the image dataset.

27. The medical device of claim 13, further comprising:
an input or output device configured to at least one of localize the imaging region of the structure or select the environment of the imaging region of the structure.

28. The medical device of claim 14, further comprising:
an input or output device configured to at least one of localize the imaging region of the structure or select the environment of the imaging region of the structure.

29. The medical device of claim 26, wherein the spatial resolution or the spectral resolution of the X-ray detector is different in the detector region for acquiring the image data for the environment of the imaging region of the structure and in a further detector region for acquiring image data for the remainder of the field of view.

30. The medical device of claim 13, wherein the medical device is a computed tomography system or a C-arm angiography system.

31. The method of claim 3, wherein:
the spatial resolution in the environment is increased relative to the spatial resolution in the remainder of the field of view by combining a plurality of values of detectors external to the assigned detector region among a plurality of detectors to form a plurality of combined detector values; and
the acquiring an image dataset includes generating the plurality of values using the plurality of detectors.

32. The method of claim 5, wherein:
the first acquisition parameter is configured to increase the spectral resolution in the environment relative to the spectral resolution in the remainder of the field of view by increasing a first quantity of energy channels of each detector in the assigned detector region among a plurality of detectors relative to a second quantity of energy channels of each detector external to the assigned detector region among the plurality of detectors; and
the acquiring an image dataset is performed using the plurality of detectors.

33. A method for local improvement of image quality of an imaging X-ray acquisition, the method comprising:
localizing an imaging region of a structure;
selecting an environment of the imaging region of the structure, the environment being a portion of a field of view;
setting, by an X-ray detector, a first acquisition parameter for the environment, the first acquisition parameter having a value different from a value of a second acquisition parameter for a remainder of the field of view exclusive of the environment, both of the first acquisition parameter and the second acquisition parameter being configured to change at least one of a spatial resolution or a spectral resolution; and
acquiring an image dataset using the first acquisition parameter.

34. The method of claim 1, wherein the first acquisition parameter has a higher value than the second acquisition parameter.

* * * * *